United States Patent [19]
Albert et al.

[11] Patent Number: 5,117,833
[45] Date of Patent: Jun. 2, 1992

[54] BI-SPECTRAL FILTERING OF ELECTROCARDIOGRAM SIGNALS TO DETERMINE SELECTED QRS POTENTIALS

[75] Inventors: David E. Albert, Oklahoma City; Paul Lander, Norman, both of Okla.

[73] Assignee: Corazonix Corporation, Oklahoma City, Okla.

[21] Appl. No.: 612,407

[22] Filed: Nov. 13, 1990

[51] Int. Cl.⁵ .......................................... A61B 5/0452
[52] U.S. Cl. .................................................. 128/702
[58] Field of Search ............................... 128/702-704, 128/699

[56] References Cited

U.S. PATENT DOCUMENTS

| | | | |
|---|---|---|---|
| 4,680,708 | 7/1987 | Ambos et al. | 128/702 |
| 4,924,875 | 5/1990 | Chamoun | 128/702 |
| 4,961,428 | 9/1990 | Nikias et al. | 128/699 |
| 4,974,162 | 11/1990 | Siegel et al. | 128/702 |
| 5,012,815 | 5/1991 | Bennett, Jr. et al. | 128/699 |

OTHER PUBLICATIONS

"Digital Filterig with Applications to Electrocardiogram Processing" by C. S. Weaver et al., IEEE Transactions on Audio and Electroacoustics, vol. AU-16, No. 3, Sep. 1968, pp. 350-391.
"Digital filtering of the e.c.g.—a comparison of low--pass digital filters on a small computer", by T. P. Taylor et al., Medical and Biological Engineering, Jul. 1974, pp. 493-502.
"Late Potentials in Man and Cardiac Arrhythmias", by M. B. Simson, Cardiovascular Section, Dept. of Medicine, University of Pennsylvania, pp. 255-264, 1981.
"Non-Invasive Recording of Late Ventricular Activity Using an Advanced Method in Patients with a Damaged Mass of Ventricular Tissue", by Shimon Abboud et al., Journal of Electrocardiology, 16 (3), 1983, pp. 245-252.
"Evaluation of Fourier Transform Filter for High-resolution ECG", David W. Christenson et al., Journal of Electrocardiology, vol. 22 Supp., pp. 33-40, 1990.
"Use of High-pass Filtering to Detect Late Potentials in the Signal-averaged ECG", by Paul Lander et al., Journal of Electrocardiology, vol. 22, Supp., pp. 7-12, 1990.
Mori et al., "Japanese Circulation Journal", vol. 32, Feb. 1968, pp. 149-160.

Primary Examiner—William E. Kamm
Attorney, Agent, or Firm—Laney, Dougherty, Hessin & Beavers

[57] ABSTRACT

Method and apparatus for analyzing electrocardiogram signals to ascertain any defects or abnormalities in heart activity. Sensed, orthogonal x, y and z input signals are processed to obtain QRS onset and then passed through first and second spectral filters having respective passbands of 70-200 hertz and 40-200 hertz in order to establish QRS offset and accurate determinations of RMS voltage values and (LAS) low amplitude signals in the terminal QRS portion of the ECG signal. A spectral filtering of the x, y and z input signals with 150-250 hertz bandpass window also allows determination of certain high frequency activity in the midportions of the QRS.

16 Claims, 3 Drawing Sheets

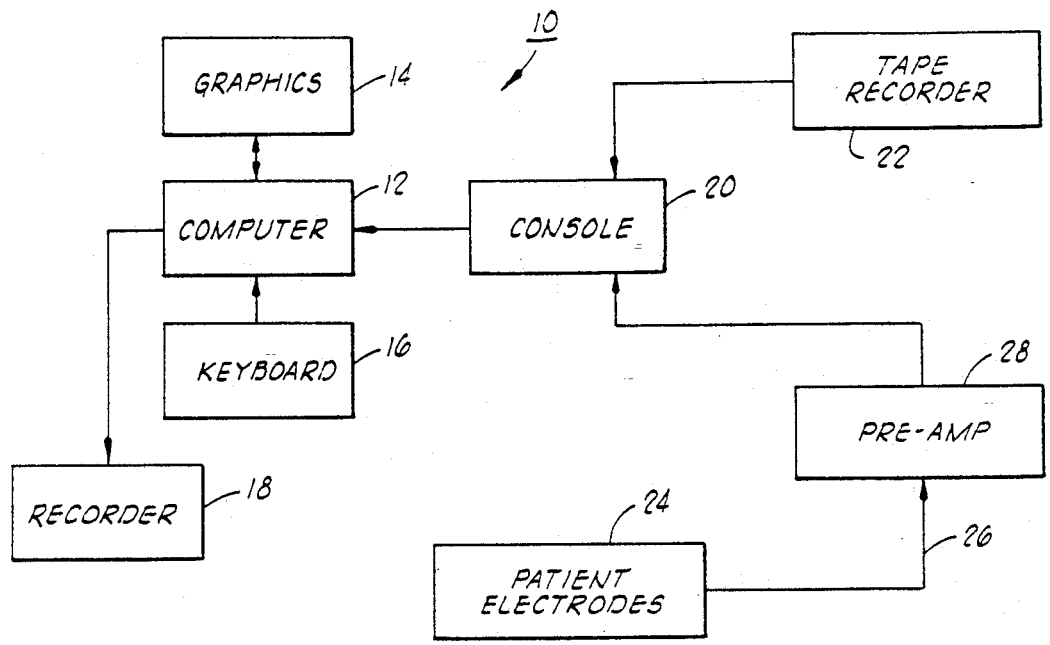
FIG. 1
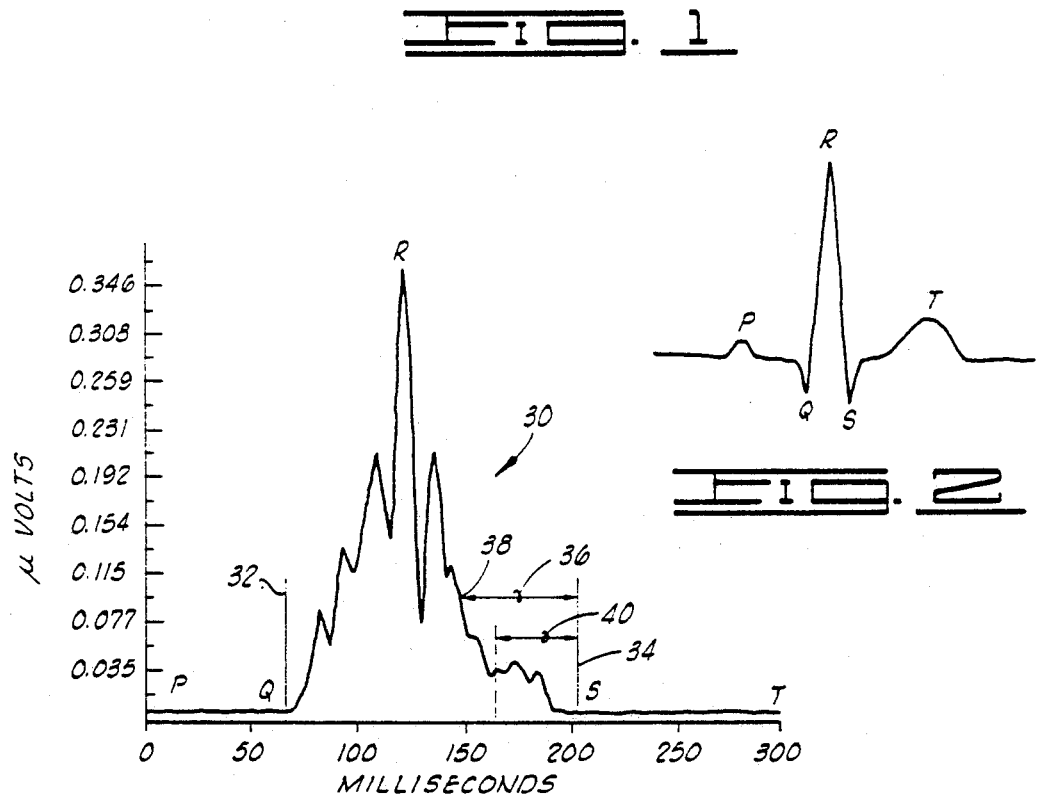
FIG. 2
FIG. 3

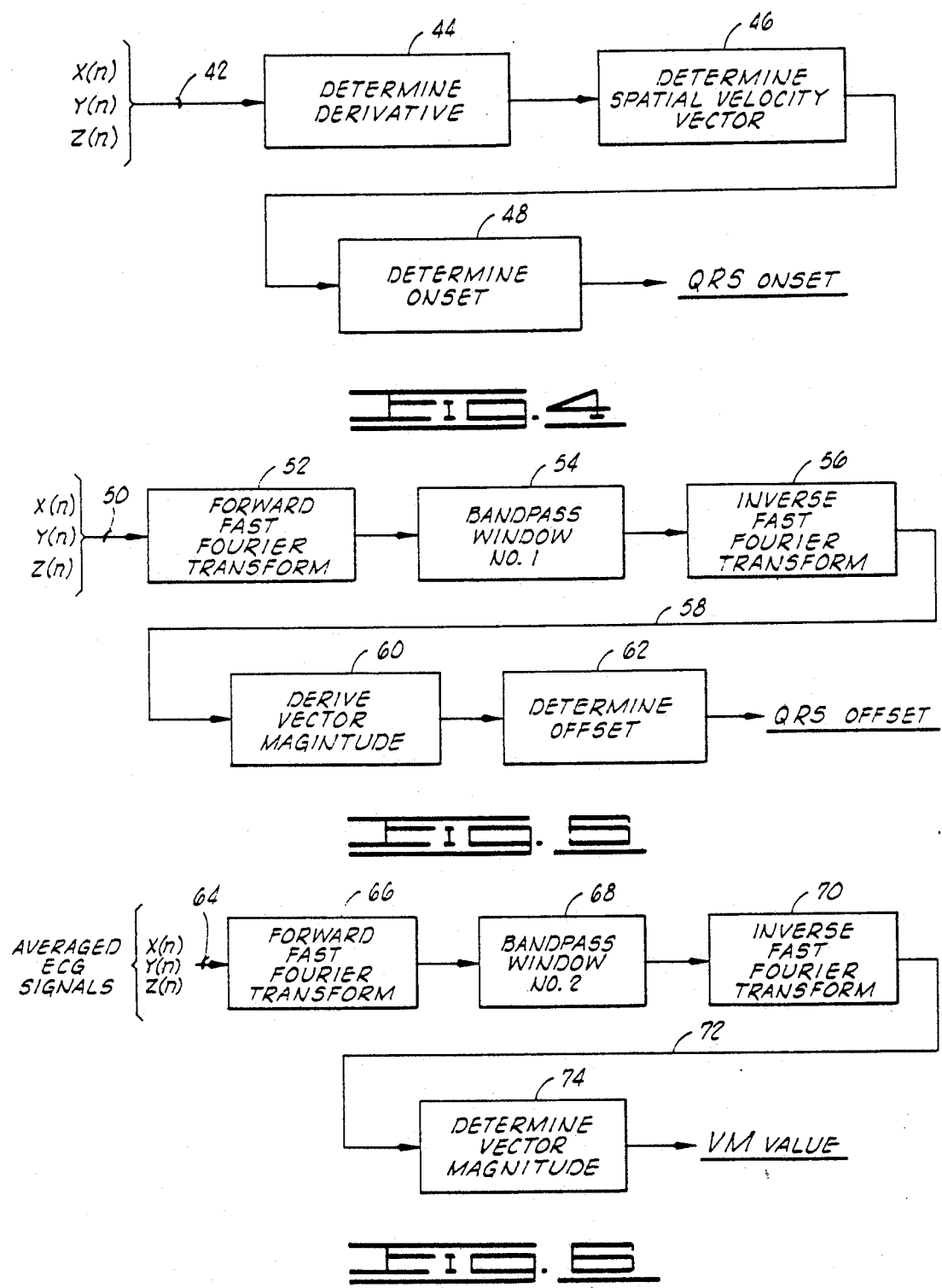

BI-SPECTRAL FILTERING OF ELECTROCARDIOGRAM SIGNALS TO DETERMINE SELECTED QRS POTENTIALS

BACKGROUND OF THE INVENTION

1. Field of the Invention

The invention relates generally to a computer implemented process for analysis of electrocardiogram signals and, more particularly, but not by way of limitation, it relates to an improved type of spectral filter for use in analyzing the electrocardiogram signal.

2. Description of the Prior Art

An early work related to the present invention is a publication entitled "Digital Filtering With Applications to Electrocardiogram Processing" by C. S. Weaver et al., IEEE Transactions on Audio and Electrocoustics; Vol. AU-16, No. 3, September, 1968, pp. 350-391. This publication discusses digital filtering in general and its possible applications to such as electrocardiogram processing. The paper discusses the design of low-pass, bandpass, high-pass, and notched filters using Z-transform techniques. The various filters are analyzed in relation to their use with the ECG wave form. A subsequent article entitled "Digital Filtering of the ECG—A Comparison of Low-Pass Digital Filters on a Small Computer" by T. P. Taylor et al.—Medical and Biological Engineering, July, 1974, pp. 493-502 discusses low-pass linear digital filters and their frequency, phase and impulse responses when used for filtering electrocardiograms.

Bi-directional digital filtering of ECG signals is described in a paper entitled "Late Potentials in Man and Cardiac Arrhythmias" by M. B. Simson et al., which appeared in Cardiovascular Section, Department of Medicine, University of Pennsylvania, pp. 255-264, 1981. An outgrowth from these basic teachings regarding the bi-directional type of digital filter is the subject matter of U.S. Pat. No. 4,422,459 in the name of M. B. Simson.

Digital filtering of electrocardiograms has also been extensively studied by an Israeli group as evidenced by the publication entitled "Non-Invasive Recording of Late Ventricular Activity Using an Advanced Method in Patients with a Damaged Mass of Ventricular Tissue" by Shimon Abboud et al. which appeared in Journal of Electrocardiology, Vol. 16, No. 3, 1983, pp. 245-252. More recent studies relate to the Fourier transform filter as analyzed in a publication entitled "Evaluation of Fourier Transform Filter for High-Resolution ECG" by D. W. Christenson et al. which appeared in Journal of Electrocardiology, Vol. 22 Supp., pp. 33-40, 1990. The FFT filter was used in connection with high-resolution electrocardiography in order to analyze the high-frequency content of ECG data to accentuate the high-frequency components thereby to enhance a new group of indicator signals.

Finally, in a publication entitled "Use of High-Pass Filtering to Detect Late Potentials in the Signal-Averaged ECG" by P. Lander and E. J. Berbari which appeared in Journal of Electrocardiology, Vol. 22, Supp. pp. 7-12, 1990, the authors analyze the various types of digital filter to derive advantages and disadvantages relative to ECG analysis. Thus, each of infinite impulse response filter (IIR), spectral window filter, and finite impulse response filter (FIR) were applied to the signal-averaged ECG to develop and analyze responses that readily disclose advantages and disadvantages of each type of filter. This study concludes that multiple filters may well be the best approach in providing full and positive analysis of the ECG waveform.

SUMMARY OF THE INVENTION

The present invention relates to an improved method and apparatus for analyzing an electrocardiogram signal utilizing plural stages of spectral filtering. ECG signals are time averaged over a selected duration whereupon the X, Y, Z and/or vector magnitude signals are further analyzed to isolate anomalies in the signal potentials within the QRS complex. A plurality of spectral filters are utilized, each with a different frequency range of bandpass window, to better isolate late potential measurements and to identify certain high frequency components that may occur during the QR duration.

Therefore, it is an object of the present invention to provide a spectral filter combination that is superior to the bi-directional filter for establishing with diagnostic accuracy the various ECG late potentials.

It is also an object of the invention to provide such improved diagnostic accuracy while still adhering to recognized industry standards.

It is still further an object of the present invention to provide spectral filters for processing the ECG signals with zero phase shift response and minimal mid-QRS signal distortion.

It is yet another object of the invention to enable analysis of the entire QRS complex to ascertain any abnormal conductions.

Finally, it is an object of the present invention to provide an ECG diagnostic method that minimizes the necessity for user over-reading of computer-derived waveform measurements.

Other objects and advantages of the invention will be evident from the following detailed description when read in conjunction with the accompanying drawings which illustrate the invention.

BRIEF DESCRIPTION OF THE DRAWINGS

FIG. 1 is a block diagram of a computer controlled system that utilizes the present invention;

FIG. 2 is a graphic representation of typical principal waves of an electrocardiogram;

FIG. 3 is a graph in microvolts versus milliseconds illustrating a cardiogram signal vector for a signal-averaged and high-pass filtered heartbeat;

FIG. 4 is a flow diagram illustrating the steps for determining QRS onset;

FIG. 5 is a flow diagram illustrating steps for determining QRS offset;

FIG. 6 is a flow diagram illustrating steps for developing a vector magnitude value.

DETAILED DESCRIPTION OF THE INVENTION

Figure 7:
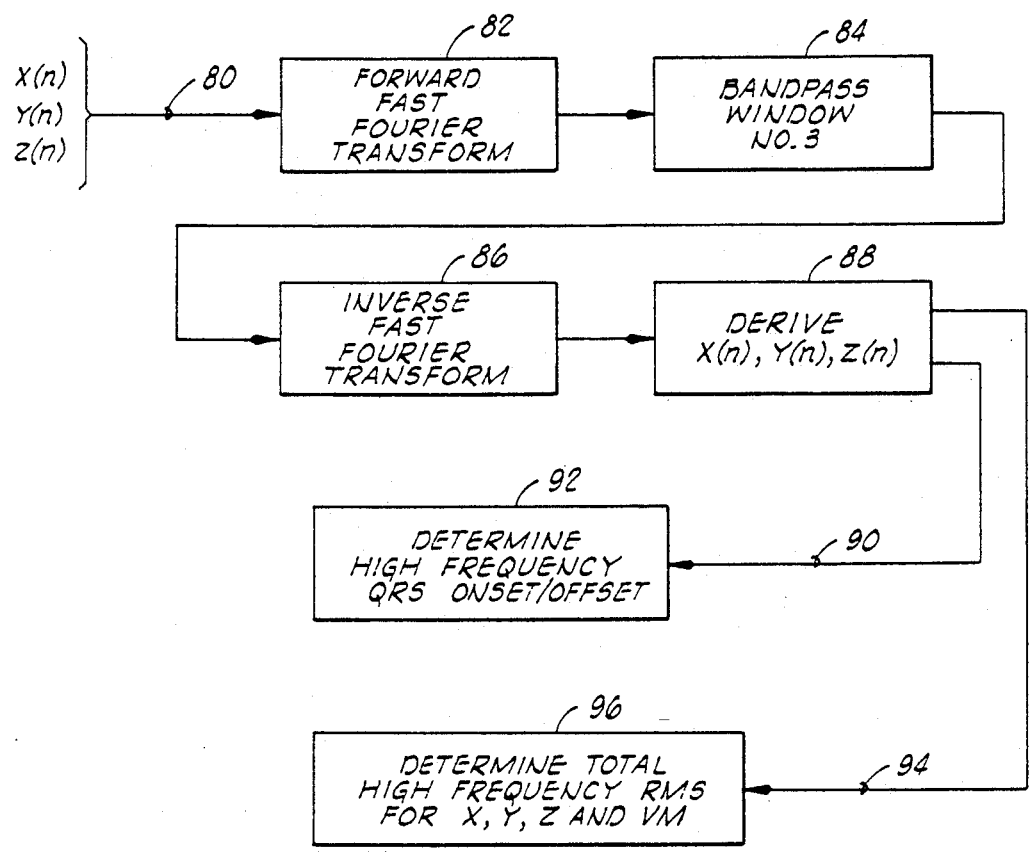
FIG. 7 is a flow diagram illustrating the steps for high frequency QRS analysis.

FIG. 1 illustrates the basic interactive components of a signal averaging ECG system 10. The system 10 is an integrated, signal-averaging electrocardiograph which is portable for non-invasive use to determine a great number of effects and analyses that may show up in the heartbeat signal. The computer 12 includes graphics screen 14 which may be an IBM type PC/AT or clone, or the Compaq III. The computer may utilize such as an 80286 microprocessor with high resolution graphics and it may utilize an 80287 math co-processor. Thirty megabytes of hard disk storage are included along with a 16 bit, 8 channel analog to digital converter. The computer 12 receives operator control through a keyboard 16 and it provides output to a recorder 18 which can be any of several types of well-known tape recorder or disk.

A console 20 generates control input to the computer 12 and may include the QRS detection hardware, amplifiers and filters for patient electrode input and high level outputs. High level inputs of pre-recorded data from such as an FM tape recorder 22 are optional. The patient electrodes 24, that is the standard form of orthogonal inputs are conducted via a cable 26 for individual amplification in a preamplifier 28, and the pre-amp 28 outputs are then applied to console 20. The data aquisition facilities provide for real-time input from patient electrodes 24. Real-time input is acquired from either three bipolar body surface ECG leads, i.e., an orthogonal X, Y, Z electrode configuration, or from 1-3 channels of high-level input from tape recorder 22. Analog signals are amplified, filtered and sampled by the computer 12. During real-time data collection, a hardware QRS detector and software correlation are employed to select only the signals desired to make up the average. Such data is then saved in data file on the computer's hard disk for subsequent analysis.

The analyzer's software allows the user to implement any number of the current late potential analysis techniques as reported in the literature. Analysis is menu driven and has print and plot routines for all graphic screens. Signal averaging is carried out to aid in distinguishing late potentials as random noise is inherently eliminated in the averaging process while valid late potential signals are enhanced. Each incoming QRS complex is transferred to the computer, which checks the uniformity of the beat, lines it up with the old average, adds each sample point to the average, and increments the total number of beats. In this way a signal average is built up over time, and when the user saves a data file the array of average points is saved along with the number of beats and other acquisition parameters. The averaging procedure is extremely effective in reducing noise and. e.g., for a 200 beat sample, the signal-to-noise ratio can be improved by as much as 23 dB.

FIG. 2 illustrates the principal waves of an ECG signal which includes the configurations identified as P, Q, R, S and T of the heartbeat. Signal anomalies in a heartbeat that may be indicative of heart damage or abnormality are brought out through various processes and FIG. 3 illustrates an ECG vector output. That is, a vector output 30 is derived by squaring each of the X, Y and Z signal values and taking the square root of their sum. This is carried out digitally for each sample point along the time axis of the signals. In FIG. 3, the curve defines the QRS complex in relation to the overall beat (PQRST). The software of the present process functions to automatically define the QRS onset at vertical bar 32 and the QRS offset at bar 34 delineating the QRS complex therebetween. The low amplitude signal portion (LAS) is defined by arrow 36 as it extends from QRS offset bar 34 to what is defined as a point 38 on the downside slope from the R peak in the complex where the vector voltage exceeds the low amplitude signals (LAS). The last forty milliseconds of the QRS complex are designated by the arrow 40 and termed the terminal QRS portion. This terminal period 40, usually but not always designated as forty milliseconds, defines a period during which several late potential parameters of interest may appear.

Digitizing of the input ECG signals may be carried out variously at pre-selected rates of sampling frequency, time window and the like. A typical set-up for receiving ECG inputs and digitizing might include a three hundred millisecond window within which the PQRST signal is set and within which 600 sampling points might be selected. Thus this would amount to two thousand samples per second per lead.

FIG. 4 shows the steps for determination of QRS onset wherein input 40 receives successive inputs of the X, Y and Z signals. Flow stage 44 then determines the derivative for each of the input ECG signals in accordance with the relationship $$x^1(n) = x(n) - x(n-1) \qquad (1)$$

$y^1(n)$ and $z^1(n)$ would be similarly determined. At flow stage 46 the spatial velocity vector SVV is determined in accordance with the relationship as follows:

$$SVV = \sqrt{x^1(n)^2 + y^1(n)^2 + z^1(n)^2} \qquad (2)$$

Given the spatial velocity vector SVV, the QRS onset or point Q of the waveform can be determined and identified in terms of point position along the total 300 millisecond (600 point) waveform. Note bar 32 in the graph of FIG. 3 which represents the QRS onset or that point at which more considerable voltage activity commences. Software within the computer 12 functions to carry out the determine onset function of stage 48.

Referring now to FIG. 5, there is utilized a first spectral filter. The orthogonal ECG signals x(n), y(n), z(n) are applied to input 50 to the spectral filter consisting of fast Fourier transform 52, bandpass window 54, 70-200 hertz, and inverse fast Fourier transform 56. This is the usual configuration for a spectral filter wherein an input waveform is Fourier-transformed to obtain its complex Fourier spectrum, and this is then multiplied by a selected frequency window function for subsequent inverse Fourier-transformation to give the filtered waveform output as is present on a line 58. Thus, each of the input ECG signals x(n), y(n), z(n) are spectral filtered with a bandpass of 70-200 hertz to develop respective X(n), Y(n) and Z(n) filtered signals for input to stage 60 to derive vector magnitude. The vector magnitude is then determined in accordance with the relationship $$VM = \sqrt{X(n)^2 + Y(n)^2 + Z(n)^2} \qquad (3)$$

and the output is applied to stage 62 which determines the QRS offset at cessation of electrical activity below a certain threshold, i.e., the offset bar 34 of FIG. 3.

FIG. 6 represents the flow for late potential measurements that utilizes a second spectral filter having a second bandpass window of 40 to 200 hertz. Thus, ECG inputs x(n), y(n) and z(n) applied to input 64 receive a fast Fourier transform 66, the output of which is processed through the 40-200 hertz bandpass window 68 and subsequent inverse fast Fourier transform 70 so that output lead 72 will convey the successive filtered ECG output signals X(n), Y(n) and Z(n). The filtered ECG signals of each lead 72 are then applied to a vector magnitude stage 74 where vector magnitude is determined in accordance with the relationship of aforementioned Equation (3). The output vector magnitude value VM is then available for further processing to aid in determination of other key indicator values across the ECG waveform.

The adoption and usage of spectral filters in FIGS. 5 and 6 was done because of recent findings by the inventors while investigating spectral hi-pass filtering of signal averaged ECG signals for evaluation of ischemia. It was discovered that computer-derived QRS durations decreased as the filter cut off frequency increased. It was then determined that filter cut off frequency at about 40 hertz resulted in an indicated QRS duration about 7 milliseconds longer than at a cut off frequency of 80 hertz which, in turn, gave a QRS duration about 7 milliseconds longer than a cut off frequency of 100 hertz. Actually, the true QRS duration is the value derived at between 70 to 80 hertz cut off frequency. The true QRS duration as measured by a 40 hertz bi-directional filter matched precisely with the duration as derived by a spectral filter with a frequency cut off of 70 to 80 hertz. While the higher cut off frequency decreased the signal amplitude, it also decreased the noise power such that the signal-to-noise ratio remained excellent. The decreased QRS signal power in the 70 to 80 hertz spectral filter high pass transition band results in elimination of filter ringing and, additionally, the zero phase shift response of the spectral filter improves the QRS offset detection by eliminating any phase shift distortion in the ST segment of the wave form.

Once QRS offset has been detected using the 70 to 80 hertz spectral filter (bandpass window 54 of FIG. 5), then the original signa may be refiltered with the 40 hertz spectral filter (bandpass window 68 of FIG. 6) and the RMS 40 and LAS values can be calculated using this filter's output together with the QRS on/offset from FIGS. 4 and 5. Resulting indicator values correlated extremely well with those previously derived using the well-known bi-directional filter (r greater than 0.97).

With the bi-spectral filter system, the total QRS duration can be determined by subtracting the time value for QRS onset as determined in FIG. 4 from the value derived for QRS offset in FIG. 5. The RMS values can be determined using the QRS offset result of FIG. 5 and the vector magnitude value derived in FIG. 6, and then calculating the terminal RMS function, i.e., the RMS voltage values for the terminal 40 milliseconds of the waveform (arrow 40 in FIG. 3). The LAS value or low amplitude signals (arrow 36 of FIG. 3) are determined using the value for QRS offset as derived in FIG. 5 and the vector magnitude as derived in FIG. 6 to identify the duration of any terminal signals beneath a selected voltage threshold, e.g., the low amplitude signals less than 40 microvolts.

A spectral filter is employed to determine yet another indicator, a high frequency filtering that effects QRS analysis to assess abnormal myocardial conduction in the beginning and middle of the QRS portion of the ECG waveform. Thus, the individual ECG signals x(n), y(n) and z(n) are input via input 80 to a spectral filter consisting of fast Fourier transform 82 bandpass window no. 3 84 (150-250 hertz) and an inverse fast Fourier transform 86. Spectral filtered data is then output for each of the orthogonal inputs at stage 88, and output on lead 90 is applied to flow stage 92 whereupon QRS onset and offset are determined in terms of high frequency response. Filtered orthogonal outputs are also applied on line 94 to flow stage 96 in order to calculate the total high frequency RMS values for the respective orthogonal waveforms as well as for their vector magnitude.

The foregoing discloses novel method and apparatus for examination of electrocardiogram signals to isolate and identify signal anomalies indicative of heart defects and abnormalities. The present system employs bi-spectral filtering within selected passbands which tend toward greater distinctiveness and reduction of noise effects to provide a more exact analysis than was previously derived using such as bi-directional filtering, IIR or FIR filter combinations, and various other types and configurations of digital filter as tried throughout the prior art. The present invention establishes that with proper selection of bandpass windows the spectral-type filter will provide superior results in isolating and identifying meaningful signals present across the electrocardiogram waveform.

Changes may be made in combination and arrangement of elements or steps as set forth in the specification and shown in the drawings; it being understood that changes may be made in the embodiments disclosed without departing from the spirit and scope of the invention as defined in the following claims.

What is claimed is:

1. A method for determining anomalous late potentials in an electrocardiogram signal, comprising:
   sensing orthogonal x, y and z electrocardiogram signals;
   deriving the first derivative value for each of said x, y and z signals;
   determining the spatial velocity vector from said first derivative x, y and z values;
   determining QRS onset for the electrocardiogram signal from the spatial velocity vector;
   spectral filtering each of the sensed x, y and z electrocardiogram signals using a first bandpass window to derive X, Y and Z filtered signals;
   generating the vector magnitude of said X, Y and Z filtered signals;
   determining QRS offset for the electrocardiogram signal using a selected one of the vector magnitude and X, Y and Z filtered signals; and
   indicating from said above-determined signals any anomalous late potentials in the QRS portion of the electrocardiogram signal.

2. A method as set forth in claim 1 which is further characterized to include:
   spectral filtering each of the sensed x, y and z electrocardiogram signals using a selected second bandpass window to derive second X, Y and Z filtered signals;
   generating the vector magnitude of said second X, Y and Z filtered signals; and
   determining and indicating discrete RMS voltage values for a selected duration of the QRS portion of the electrocardiogram signal.

3. A method as set forth in claim 2 wherein:
   said second bandpass window is in the range from 40 to 200 hertz.

4. A method as set forth in claim 2 which is further characterized to include:
   spectral filtering each of the x, y and z electrocardiogram signals using a third bandpass window extending from 150 to 250 hertz to derive X, Y and Z high frequency filtered signals; and
   detecting and indicating high frequency activity in the middle of the QRS portion of the electrocardiogram signal.

5. A method as set forth in claim 4 wherein:
said first bandpass window is in the range from 70 to 200 hertz.

6. A method as set forth in claim 5 wherein:
said second bandpass window is in the range from 40 to 200 hertz.

7. A method as set forth in claim 4 wherein:
said first bandpass window is in the range from 80 to 200 hertz.

8. A method as set forth in claim 7 wherein:
said second bandpass window is in the range from 40 to 200 hertz.

9. A method as set forth in claim 1 wherein:
said first bandpass window is the range from 70 to 200 hertz.

10. A method as set forth in claim 9 wherein:
said second bandpass window is in the range from 40 to 200 hertz.

11. A method as set forth in claim 1 wherein:
said first bandpass window is in the range of from 80 to 200 hertz.

12. A method as set forth in claim 11 wherein:
said second bandpass window is in the range of from 40 to 200 hertz.

13. A method as set forth in claim 1 which is further characterized to include:
spectral filtering each of the x, y and z electrocardiogram signals using a third bandpass window extending from 150 to 250 hertz to derive X, Y and Z high frequency filtered signals; and
detecting and indicating high frequency activity in the middle of the QRS portion of the electrocardiogram signal.

14. A method as set forth in claim 13 wherein:
said first bandpass window is the range from 70 to 200 hertz.

15. A method as set forth in claim 14 wherein:
said second bandpass window is in the range from 40 to 200 hertz.

16. A method as set forth in claim 13 wherein:
said first bandpass window is in the range from 80 to 200 hertz.

* * * * *